(12) United States Patent
Zhao et al.

(10) Patent No.: US 10,540,549 B2
(45) Date of Patent: Jan. 21, 2020

(54) SYSTEMS AND METHODS OF PROVIDING DECISION SUPPORT TO FIRST RESPONDERS

(71) Applicant: MOTOROLA SOLUTIONS, INC., Chicago, IL (US)

(72) Inventors: Kang-Kai Zhao, SiChuan (CN); Jian-Xiang Wang, SiChuan (CN); Dong Zhao, SiChuan (CN)

(73) Assignee: MOTOROLA SOLUTIONS, INC., Chicago, IL (US)

( * ) Notice: Subject to any disclaimer, the term of this patent is extended or adjusted under 35 U.S.C. 154(b) by 300 days.

(21) Appl. No.: 15/535,803

(22) PCT Filed: Aug. 1, 2016

(86) PCT No.: PCT/CN2016/092725
§ 371 (c)(1),
(2) Date: Jun. 14, 2017

(87) PCT Pub. No.: WO2018/023339
PCT Pub. Date: Feb. 8, 2018

(65) Prior Publication Data
US 2018/0336413 A1    Nov. 22, 2018

(51) Int. Cl.
*G06K 9/00* (2006.01)
*H04W 4/90* (2018.01)
(Continued)

(52) U.S. Cl.
CPC ..... *G06K 9/00671* (2013.01); *G06K 9/00288* (2013.01); *G06K 9/00684* (2013.01);
(Continued)

(58) Field of Classification Search
CPC ................................. G06K 9/00671
See application file for complete search history.

(56) References Cited

U.S. PATENT DOCUMENTS

| 4,857,912 A * | 8/1989 | Everett, Jr. ............ G08B 19/00 340/508 |
| 7,299,152 B1 * | 11/2007 | Moritz ................... G08B 19/00 340/573.1 |

(Continued)

FOREIGN PATENT DOCUMENTS

| CN | 101404107 | 4/2009 |
| CN | 104506382 | 4/2015 |
| WO | WO-2015091065 A1 * | 6/2015 ............. G06Q 10/06 |

OTHER PUBLICATIONS

GB1900829.1 Examination Report from the United Kingdom Intellectual Property Office dated Apr. 11, 2019 (5 pages).
(Continued)

*Primary Examiner* — Dave Czekaj
*Assistant Examiner* — Shanika M Brumfield
(74) *Attorney, Agent, or Firm* — Michael Best & Friedrich LLP

(57) ABSTRACT

A method and system of providing decision support to first responders. One method includes identifying, with an electronic processor, a first plurality of characteristics of a first responder. The method further includes generating, with the electronic processor, a first score for the first responder based on the first plurality of characteristics. The method further includes identifying with the electronic processor, a suspect at an incident area. The method further includes identifying, with the electronic processor, a second plurality of characteristics of the suspect. The method further includes generating, with the electronic processor, a second score for the suspect based on the second plurality of characteristics. The method further includes comparing, with the electronic processor, the first score and the second score. The method
(Continued)

further includes outputting, with an output device electrically connected to the electronic processor, a recommended action.

15 Claims, 8 Drawing Sheets

(51) Int. Cl.
*G06N 5/04* (2006.01)
*G06Q 50/26* (2012.01)
*H04W 84/18* (2009.01)

(52) U.S. Cl.
CPC ............ *G06K 9/00718* (2013.01); *G06N 5/04* (2013.01); *G06Q 50/26* (2013.01); *H04W 4/90* (2018.02); *H04W 84/18* (2013.01)

(56) References Cited

U.S. PATENT DOCUMENTS

| | | | |
|---|---|---|---|
| 9,152,931 B2 | 10/2015 | Badaloo et al. | |
| 10,165,073 B1* | 12/2018 | Parampottil | H04L 67/22 |
| 2004/0044553 A1* | 3/2004 | Lambert | A62B 99/00 702/2 |
| 2005/0264412 A1* | 12/2005 | Levesque | G08B 21/10 340/517 |
| 2009/0177615 A1* | 7/2009 | Angell | G06N 5/04 706/53 |
| 2014/0067656 A1* | 3/2014 | Cohen Ganor | G06Q 50/01 705/39 |
| 2015/0279372 A1* | 10/2015 | Papierman | G10L 17/22 704/273 |
| 2016/0163186 A1* | 6/2016 | Davidson | G06Q 50/16 340/506 |
| 2016/0377381 A1* | 12/2016 | Lyren | F41G 3/04 345/633 |

OTHER PUBLICATIONS

PCT/CN2016/092725 International Search Report and Written Opinion of the International Searching Authority dated Apr. 28, 2017 (8 pages).

* cited by examiner

| | CHARACTERISTIC | SCORE |
|---|---|---|
| ARMED WITH WEAPON (BASE SCORE 20) | PHYSICAL CONDITION GOOD | +1 |
| | PHYSICAL CONDITION BAD (INJURED) | -10 |
| | STRONG AND TALL | +3 |
| | ARMED WITH KNIFE | +5 |
| | ARMED WITH GUN | +20 |
| | KONG FU MASTER | +10 |
| | AVERAGE KONG FU | +3 |
| | VIOLENCE TENDENCY | +10 |

FIG. 6

| PUBLIC SAFETY OFFICER OFFENSIVE SCORE | | |
|---|---|---|
| SOURCE | CHARACTERISTIC | SCORE |
| PUBLIC SAFETY INFORMATION | 170CM (HEIGHT), 150KG (WEIGHT) | 0 |
| PUBLIC SAFETY INFORMATION | KARATE, BLUE BELT | +3 |
| REAL-TIME INFORMATION FROM PAN SENSOR 235 | PHYSICAL CONDITION: GOOD | +1 |
| REAL-TIME INFORMATION FROM PAN SENSOR 235 | HOLDING GUN, WITH 10 BULLETS | +20 |
| | | TOTAL SCORE = 44 (BASE SCORE 20) |

FIG. 7A

| SUSPECT OFFENSIVE SCORE | | |
|---|---|---|
| SOURCE | CHARACTERISTIC | SCORE |
| CRIMINAL INFORMATION | 200CM (HEIGHT), 150KG (WEIGHT) | +3 |
| SOCIAL NETWORK INFORMATION | KARATE, BLACK BELT | +10 |
| CRIMINAL INFORMATION | VIOLENT CRIME BEFORE | +10 |
| REAL-TIME INFORMATION FROM FIRST CAMERA 120 | HOLDING GUN | +20 |
| REAL-TIME INFORMATION FROM COMMUNICATION DEVICE 105 | PHYSICAL CONDITION: GOOD | +10 |
| SOCIAL MEDIA INFORMATION | EXTREMIST | 0 |
| | | TOTAL SCORE = 73 (BASE SCORE 20) |

FIG. 7B

SYSTEMS AND METHODS OF PROVIDING DECISION SUPPORT TO FIRST RESPONDERS

BACKGROUND OF THE INVENTION

First responders and other public safety personnel (for example, police officers, firefighters, paramedics and the like) often have to make decisions regarding how to react and respond to a variety of situations. In many cases, first responders make such decisions based on then own observations, even though other information may be relevant to the decisions.

BRIEF DESCRIPTION OF THE SEVERAL VIEWS OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

FIG. 6 is an exemplary table that illustrates how an electronic processor may generate scores for the first responder and the suspect based on their characteristics.

FIG. 7A is a table that illustrates an exemplary first score for the first responder.

FIG. 7B is a table that illustrates an exemplary second score for the suspect.

Figure 1:
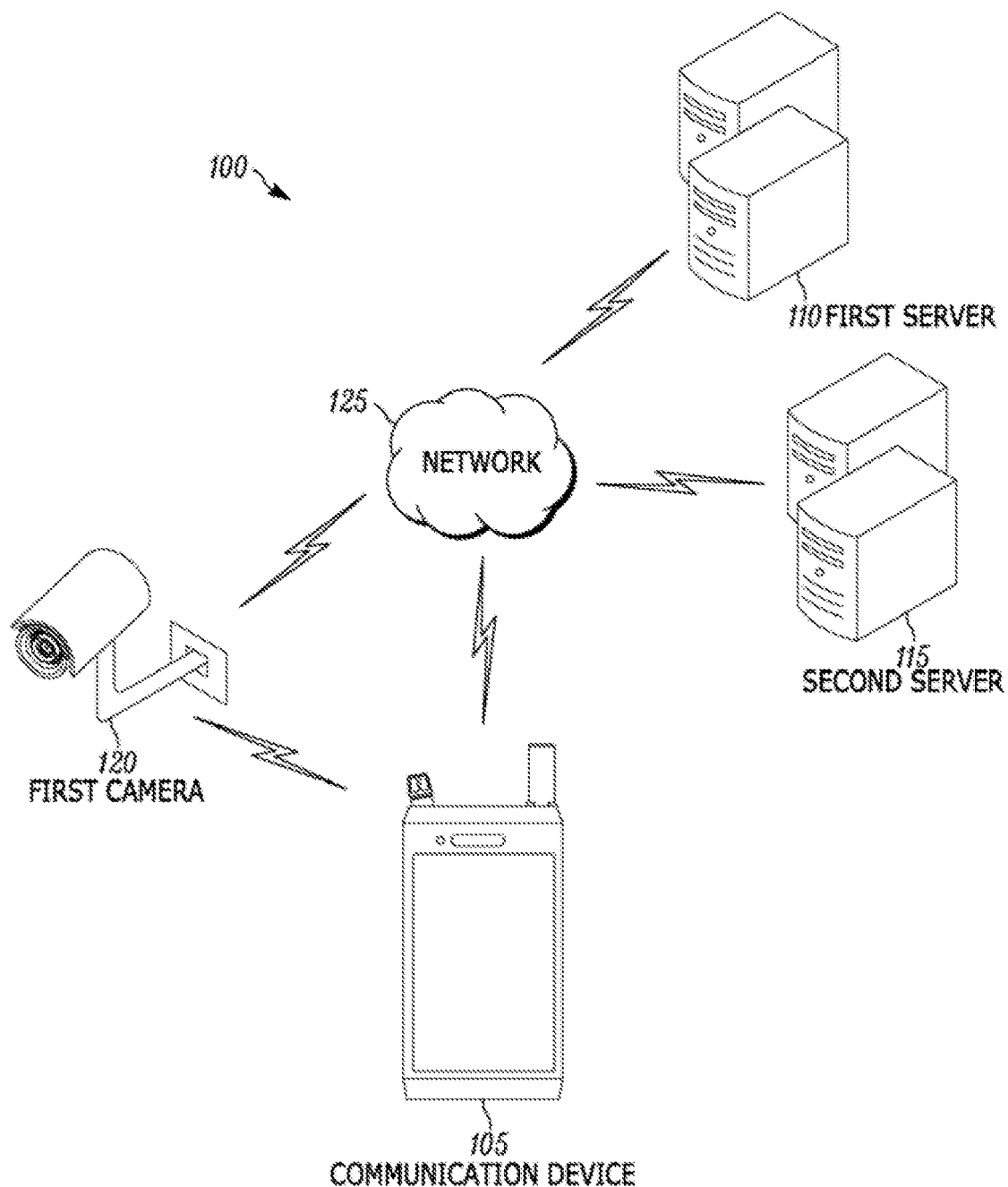
FIG. 1 is a diagram of a communication system according to one exemplary embodiment.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION OF THE INVENTION

One embodiment provides a method of providing decision support to first responders. The method includes identifying, with an electronic processor, a first plurality of characteristics of a first responder. The method further includes generating, with the electronic processor, a first score for the first responder based on the first plurality of characteristics. The method further includes identifying, with the electronic processor, a suspect at an incident area. The method further includes identifying, with the electronic processor a second plurality of characteristics of the suspect. The method further includes generating, with the electronic processor, a second score for the suspect based on the second plurality of characteristics. The method further includes comparing, with the electronic processor, the first score and the second score. The method further includes outputting, with an output device electrically connected to the electronic processor, a recommended action.

Another embodiment provides a communication device that includes a memory, a network interface an output device, and an electronic processor. The electronic processor is configured to identity a first plurality of characteristics of a first responder. The electronic processor is further configured to generate a first score for the first responder based on the first plurality of characteristics. The electronic processor is further configured to identify a suspect at an incident area, and identify a second plurality of characteristics of the suspect. The electronic processor is further configured to generate a second score for the suspect based on the second plurality of characteristics. The electronic processor is further configured to compare the first score and the second score, and transmit an electrical signal to the output device. The output device outputs a recommended action based on the electrical signal.

Another embodiment provides a method of providing decision support to first responders. The method includes receiving, with a network interface, an incident type from a communication device, the incident type having been selected on a display of the communication device. The method further includes identifying, with an electronic processor and based on the incident type, a first plurality of characteristics of a first responder. The method further includes generating, with the electronic processor, a first score for the first responder based on the first plurality of characteristics. The method further includes identifying, with the electronic processor and based on the incident type, a second plurality of characteristics of an incident. The method further includes generating, with the electronic processor, a second score for the incident based on the second plurality of characteristics. The method further includes comparing, with the electronic processor, the first score and the second score. The method further includes transmitting, with the network interface, a recommended action to the communication device, the recommended action being output by an output device of the communication device.

FIG. 1 is a diagram of a communication system 100 according to one exemplary embodiment. The communication system 100 includes a communication device 105, a first server 110, a second server 115, and a first camera 120. In some embodiments, the communication device 105 is carried and used by a public safety officer (for example, a police officer, a firefighter, a paramedic, and the like. For example, the communication device 105 may be a cellular telephone, a portable radio, a mobile radio mounted in or on a vehicle a tablet a smart watch, and the like. In some embodiments, the first server 110 is a computer maintained by public safety personnel (for example, at a public safety command center). In some embodiments, the second server 115 is a computer maintained by a third party (for example, an organization running a social media platform). In some embodiments, the first camera 120 is a camera mounted on or in a budding (for example, a pan-tilt-zoom camera). In some embodiments, the first camera 120 is mounted in or on a public safety vehicle.

In addition to the components already discussed, in some embodiments, the communication system 100 includes a network 125. The communication device 105, the first server 110, the second server 115, and the first camera 120 communicate with each other over the network 125. The network 125 may be a wired or a wireless communication network. All or parts of the network 125 may be implemented using various existing networks, for example, a cellular network, the Internet, a land mobile radio (LMR) network, a Bluetooth™ network, a wireless local area network (for example, Wi-Fi), a wireless accessory Personal Area Network (PAN), a Machine-to-machine (M2M) autonomous network, and a public switched telephone network. The network 125 may also include future developed networks. Although FIG. 1 shows only one of each of the communication device 105, the first server 110, the second server 115, and the first camera 120, additional communication devices, servers, and cameras may be included in the communication system 100 and may communicate over the network 125. In some embodiments, the communication device 105 communicates with other communication devices over the network 125 (for example, communication devices carried by other public safety personnel and mobile communication devices mounted in public safety vehicles). In some embodiments, the communication device 105 communicates with at least one of the first camera 120 and the other communication devices using an ad-hoc network or through direct links, for example, a two-way radio channel.

Figure 2A:
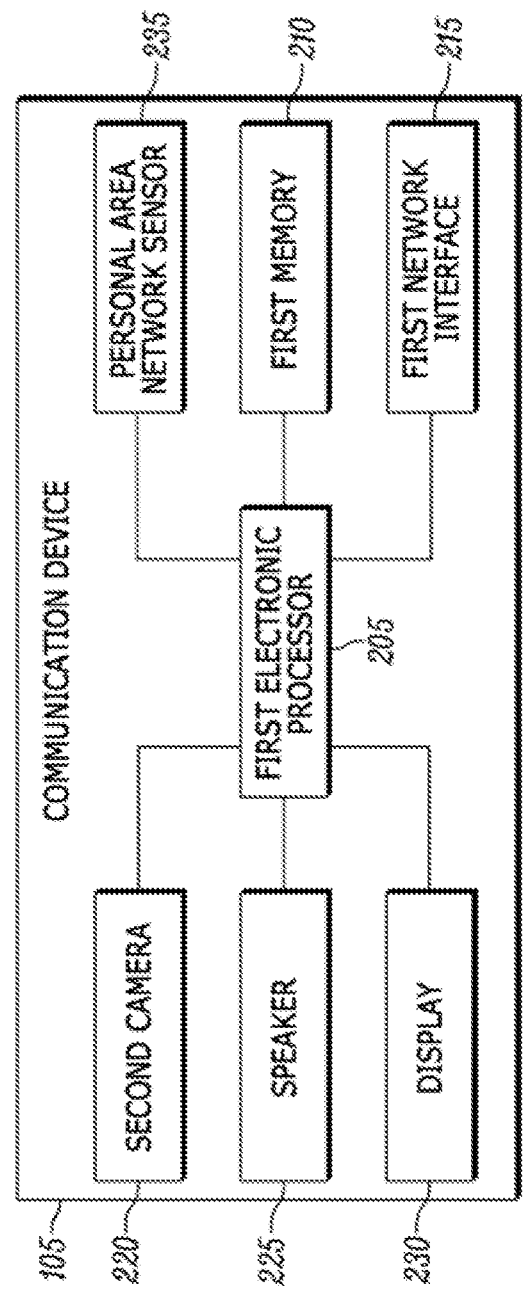
FIG. 2A is a block diagram of a communication device included in the communication system of FIG. 1 according to one exemplary embodiment.

FIG. 2A is a block diagram of the communication device 105 according to one exemplary embodiment. As illustrated in FIG. 2A, the communication device 105 includes a first electronic processor 205 (for example, a microprocessor, an application-specific integrated circuit (ASIC), or another electronic device), a first memory 210, a first network interface 215, a second camera 220, a speaker 225, a display 230, and a personal area network (PAN) sensor 235. In some embodiments, the communication device 105 includes fewer or additional components in configurations different from that illustrated in FIG. 2A. For example in some embodiments, the communication device 105 includes a transceiver to communicate with other communication devices, servers, cameras, or a combination thereof using a communication channel or connection that is outside of the network 125. In some embodiments, the communication device 305 includes a global positioning system (GPS) unit or a similar component that determines the geographic coordinates of the location of the communication device 105. In some embodiments, the communication device 105 performs functionality other than the functionality described below.

The first memory 210 may include read only memory (ROM), random access memory (RAM), other non-transitory computer-readable media, or a combination thereof. The first electronic processor 205 is configured to receive instructions and data from the first memory 210 and execute, among other things, the instructions. In particular, the first electronic processor 205 executes instructions stored in the first memory 210 to perform the methods described herein. For example, the first electronic processor 205 is configured to provide decision support to first responders.

The first network interface 215 sends and receives data to and from the network 125. For example, the first network interface 215 may include a transceiver for wirelessly communicating with the network 125. The first electronic processor 205 receives image data generated by the second camera 220 and may communicate the image data over the network 125 through the first network interface 215, such as for receipt by another communication device 105, the first server 110, or another external device. The first electronic processor 205 may receive data from the network 125 through the first network interface 215, such as from the first server 110, the second server 115, the first camera 120, or another external device. The first electronic processor 205 may output data received via the first network interface 215 from the network 125 using the speaker 225, the display 230, another output device, or a combination thereof.

In some embodiments, the second camera 220 is coupled to the communication device 105. In some embodiments, a field of view of the second camera 220 is adjusted either by an electrical signal front the first electronic processor 205 or manually by a user of the communication device 105. In some embodiments, the second camera 220 may be physically separate from the communication device 105 and may be communicatively coupled to the first electronic processor 205. For example, in some embodiments, the communication device 105 is a portable radio carried by a person such as public safety personnel and the second camera 220 is an accessory mounted on an article worn by the person (for example, a jacket, a vest, a helmet, and the likes. In another example, in some embodiments, the communication device 105 is a mobile radio mounted inside a public safety vehicle (for example, a police vehicle) and the second camera 220 is mounted within or on the public safety vehicle. In embodiments where the second camera 220 is physically separate from the communication device 105, the first electronic processor 205 may control the second camera 220 via a wired or wireless communication link. In such embodiments, the second camera 220 is considered to be part of the communication device 105 even though the components are physically separated. In some embodiments, the communication device 105 includes multiple second cameras 220 that are controlled by the first electronic processor 205. For example, the communication device 105 may include two opposed cameras (which in one example may be located one hundred eighty degrees front one another).

In some embodiments, the display 230 is a touch-sensitive display that includes both a display device (for example, a liquid crystal display (LCD) screen panel) and a user input device (for example, the touch-sensitive component that detects contact by a stylus of finger). The first electronic processor 205 may receive input signals front the display 230 that are generated by a user of the communication device 105. The first electronic processor 205 may also control content of the display 230 (for example, by presiding a graphical user interface on the display 230). In some embodiments, the personal area network sensor 235 provides real-time information about a public safety officer carrying the communication device 105. For example, in some embodiments, the personal area network sensor 235 determines whether the public safety officer is armed or unarmed by detecting the presence of a gun or other weapon. As another example, in some embodiments, the personal area network sensor 235 determines an amount of fuel remaining in a public safety vehicle of the public safety officer.

Figure 2C:
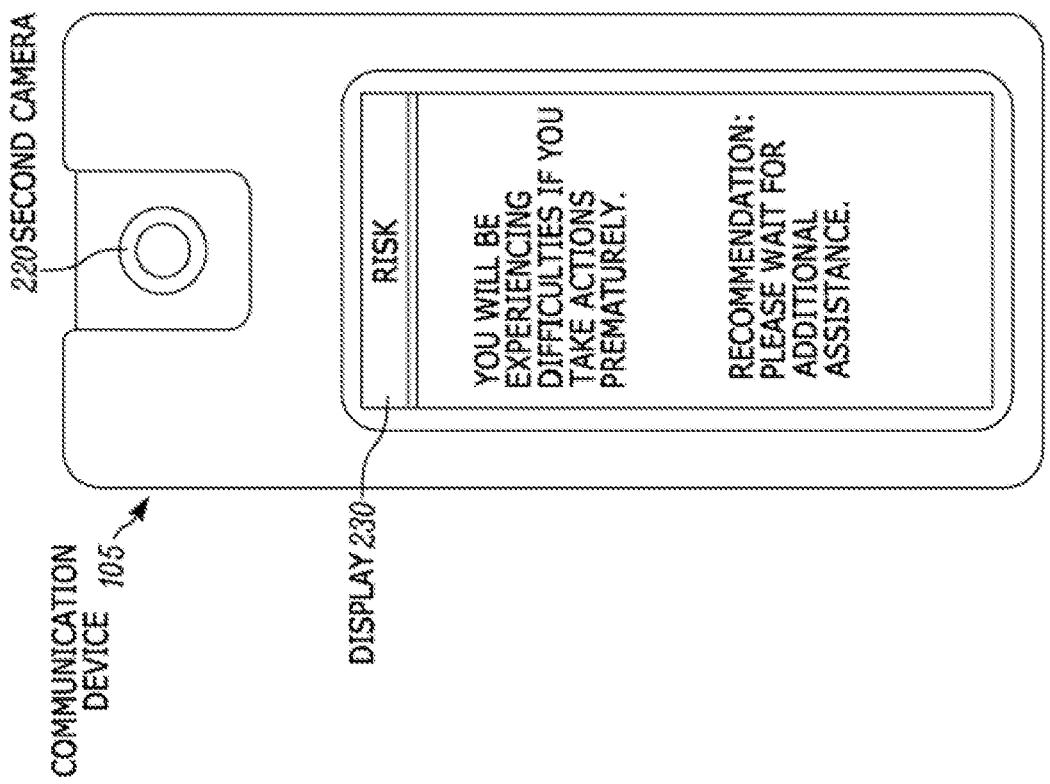
FIGS. 2B and 2C illustrate the communication device of FIG. 2A according to one exemplary embodiment.
Figure 2B:
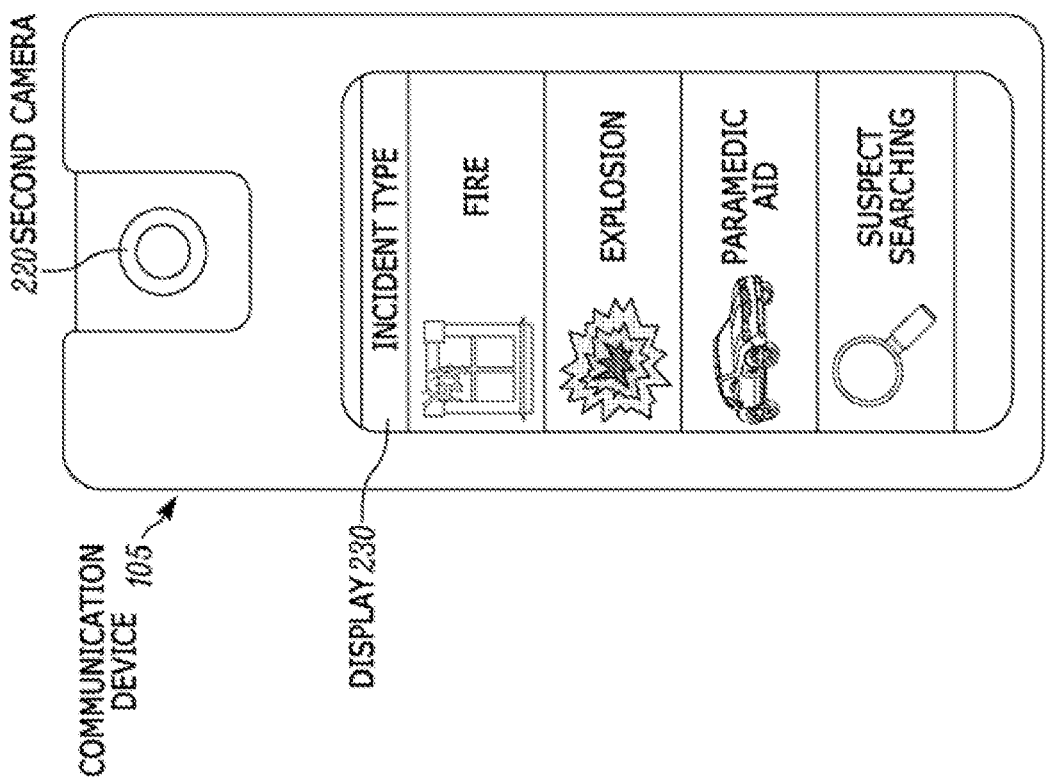

FIGS. 2B and 2C illustrate the communication device 105 including the second camera 220 and the display 230 with two different graphical user interfaces displayed. The display 230 of FIG. 2B illustrates an exemplary list of incident types to be selected by a public safety officer as will be described hereinafter. The display 230 of FIG. 2C illustrates an exemplary recommended action determined by the first electronic processor 205 as will be described hereinafter.

Figure 3:
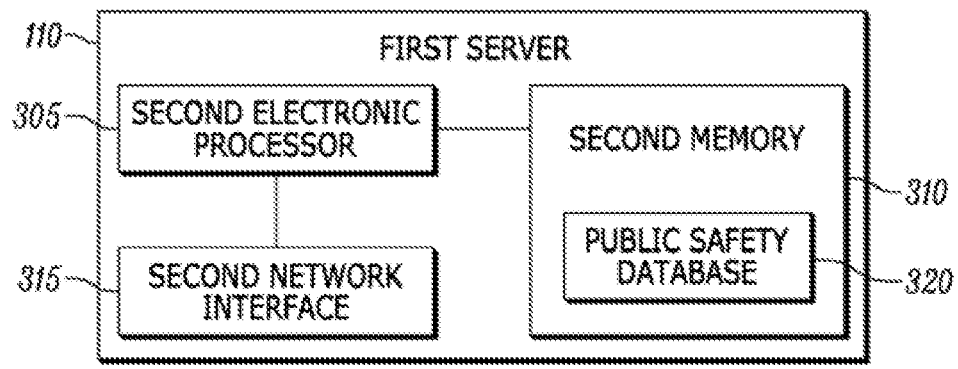
FIG. 3 is a block diagram of a first server included in the communication system of FIG. 1 according to one exemplary embodiment.

FIG. 3 is a block diagram of the first server 110 according to one exemplary embodiment. The first server 110 includes a second electronic processor 305, a second memory 310, and a second network interface 315. These components are similar to those described above with respect to the communication device 105 and perform similar functions. In some embodiments, the second memory 310 includes a public safety database 320 that includes public safety information relating to public safety personnel and criminal information relating to people who have been charged with one or more crimes (in other words, criminal records). For example, the public safety database 320 may store public safety information including, but not limited to, a title, a height, a weight, a historical record, an experience level, and a skill level of a plurality of public safety personnel. The public safety database 320 may also store criminal information including, but not limited to, a height, a weight, previous charges of crimes, and previous convictions of crimes of a suspect. In some embodiments, the first server 150 may be a communication device similar to the communication device 105 (for example, a master communication device that stores or has access to public safety information as explained previously herein).

In some embodiments, the second server 115 is a computer that includes similar components as described above with respect to the first server 110. However, a memory of the second server 115 may include a social media database for multiple social media databases) instead of the public safety database 320. In some embodiments, the social media database stores social media information including, but not limited to, people associated with each other on social media, interests of one or more people on social media, content generated by one or more people on social media, and photographs posted on social media. In some embodiments, the second server 115 is a device that provides access to one or more sources of social media information via the network 125 or via another network similar to the network 125. In some embodiments, the communication system 100 includes multiple second servers 115 that allow multiple social media databases to be accessible via the network 125.

The methods described below are used to provide decision support to public safety personnel who are first responders at an incident (for example, a location where a suspect is committing or has committed a crime, a fire, an explosion, and the like). The first responder often decides whether to take immediate action or wait for additional assistance (in other words, back-up from one or more public safety officers). When the first responder decides to take immediate action, the first responder decides what type of action is taken. The methods described below provide decision support to first responded by retrieving and evaluating information that may not be known or readily apparent to the first responder making these decisions.

Figure 4:
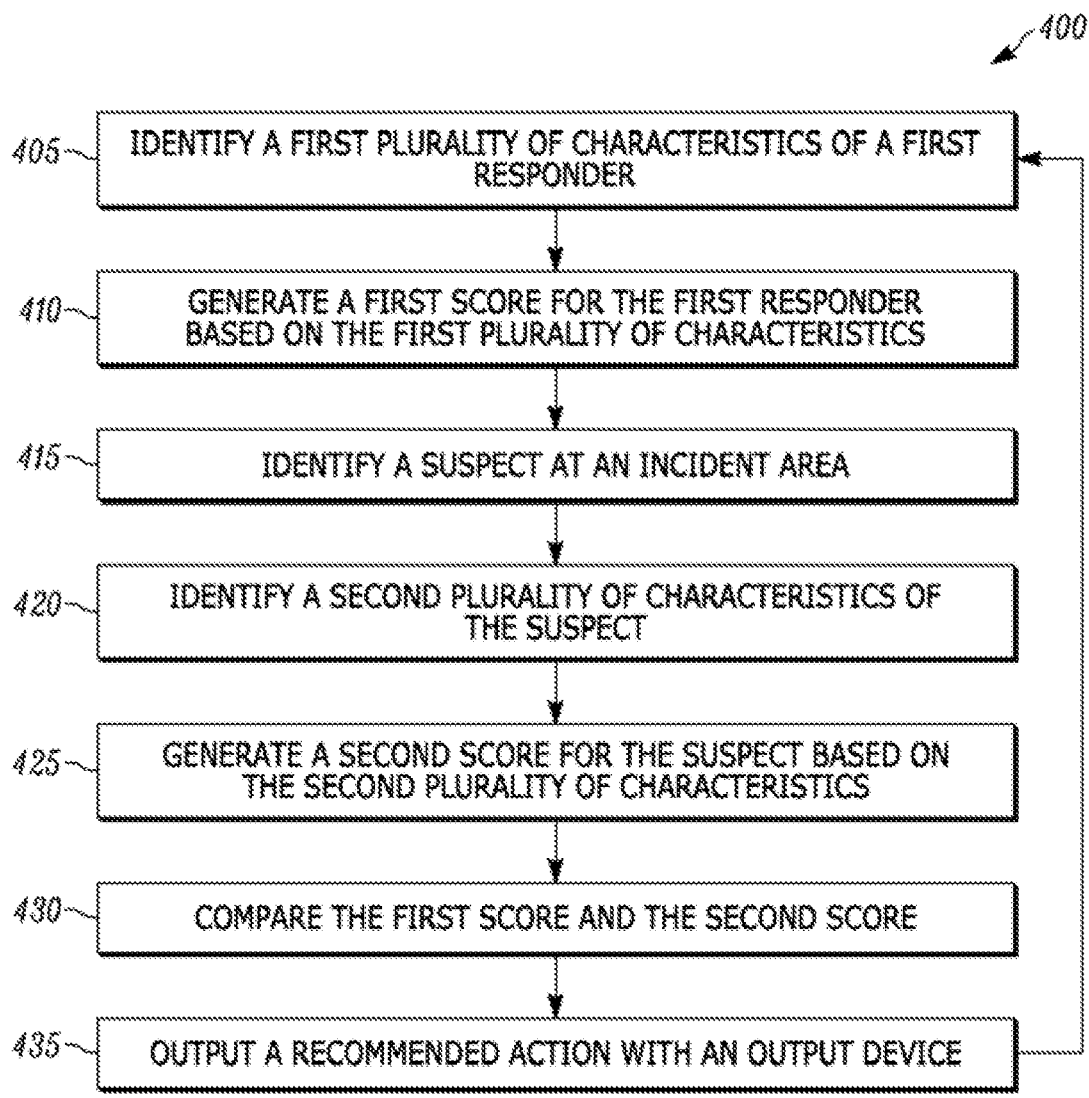
FIG. 4 is a flowchart of a method of providing decision support to first responders performed by the communication device of FIGS. 2A through 2C according to one exemplary embodiment.

FIG. 4 illustrates a method 400 of providing decision support to first responders. In some embodiments, the method 400 is executed by the first electronic processor 205 of the communication device 105. At block 405, the first electronic processor 205 identifies a first plurality of characteristics of a first responder. For example, in some embodiments, the first electronic processor 205 receives an electrical signal from the display 230 (for example, as a result of selecting an icon displayed on a graphical riser interface) that indicates that the first responder is trying to decide whether to engage a suspect (in other words, whether the first responder should, for example, retreat from the suspect, verbally confront the suspect without using force, or use force against the suspect). For example, the first responder may make such a decision when a robbery is occurring, while executing an arrest warrant while investigating an assault, and the like. For example, with reference to FIG. 2B, the public safety officer may select "Suspect Searching" on the display 230 when the public safety officer is tiding to decide whether to engage the suspect. In this exemplary embodiment, the first electronic processor 205 identifies the first plurality of characteristics to be offensive characteristics (for example, characteristics useful in actively subduing a suspect), defensive characteristics (for example, characteristics useful in thwarting an attack by a suspect) speed characteristics, and experience characteristics of the first responder.

In some embodiments, the offensive characteristics of the first responder include but are not limited to, a height, a weight, a physical condition (in other words, a strength level, a cardiovascular stamina level, whether the first responder is injured, and the like), a skill level (for example, a skill level in one or more forms of martial arts), and whether the first responder is in possession of a weapon (for example, a knife, a gun, and the like). In some embodiments, the defensive characteristics of the first responder include, but are not limited to a height, a weight, a physical condition, a skill level, an amount of armor of other protection worn by the first responder, and whether the first responder is in possession of a weapon. In some embodiments, the speed characteristics include, but are not limited to, a physical condition of the first responder and whether the first responder is using or has access to transportation (for example, a bicycle, a vehicle, a helicopter, public transportation, and the like). In some embodiments, the experience characteristics include, but are not limited to, a number of years that the first responder has been a public safety officer and a number of incidents that the first responder has handled that are similar to the present incident.

After the first electronic processor 205 identifies the first plurality of characteristics of the first responded at block 410, the first electronic processor 205 generates a first score for the first responder based on the first plurality of characteristics. In some embodiments, the first electronic processor 205 determines a score for each of the first plurality of characteristics based on at least one of the public safety information from the public safety database 320 and image data from the first camera 120. For example, in some embodiment, when the first electronic processor 205 receives the electrical signal from the display 230 that indicates that the first responder is trying to decide whether to engage the suspect, the first electronic processor 205 begins gathering information from numerous sources.

Figure 5A:
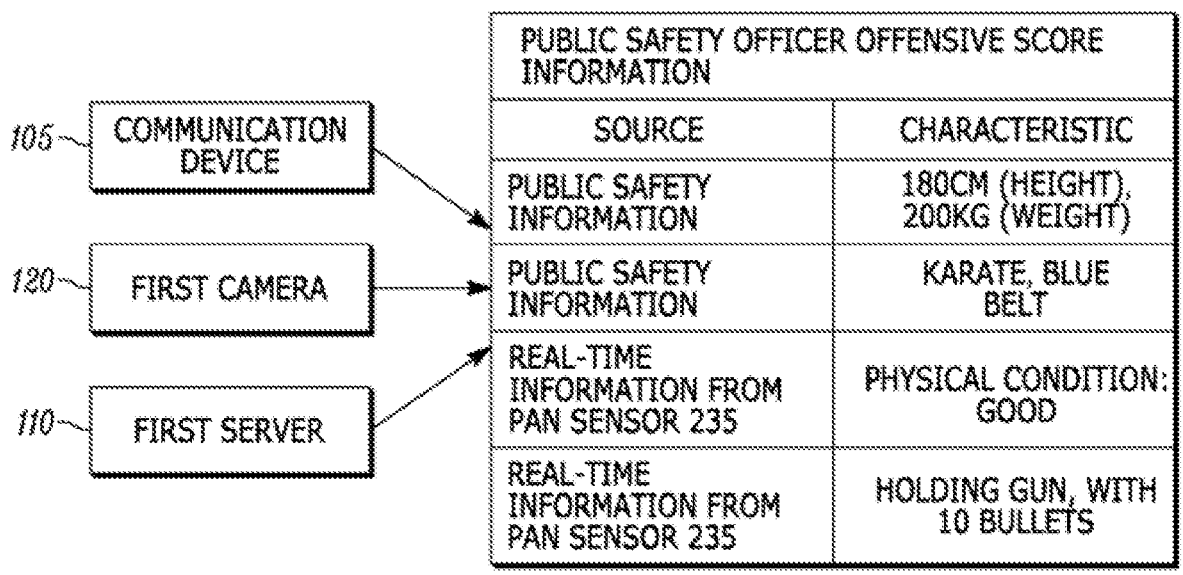
FIG. 5A is a block diagram that illustrates an exemplary table of a first plurality of characteristics of a first responder.

FIG. 5A is a block diagram that illustrates an exemplary table of the first plurality of characteristics determined by the first electronic processor 205. As shown in FIG. 5A, the first electronic processor 205 may generate the table of the first plurality of characteristics based on at least one of real-time information from the communication device 105 (for example, at least one of image data from the second camera 220 information from the personal area network sensor 255, and information entered by a public safety officer on the display 230), real-time information from other sources (for example, image from the first camera 120), and public safety information from the first server 110. For example, in some embodiments, the first electronic processor 205 sends a request for information via the first network interface 215 to the first server 110. For example, the first electronic processor 205 may request one or more characteristics of the first responder from the public safety database 320. In some embodiments, the first electronic processor 205 also determines one or more characteristics of the first responder using the personal area network sensor 235 as described previously (for example, whether the public safety officer is armed or unarmed). The first electronic processor 205 may also send a request via the first network interface 215 to the first camera 120 to receive image data from the first camera 120. Upon receiving the image data via the first network interface 215 from the first camera 120, the first electronic processor 205 may use a video analytics engine to determine one or more characteristics of the first responder. For example, in some embodiments, the video analytics engine determines whether the first responder possesses a weapon or whether the first responder is injured.

The first electronic processor 205 then generates the first score based on the characteristics of the first responder. FIG. 6 illustrates an exemplary table that shows how the first electronic processor 205 may generate scores based on characteristics. The first electronic processor 205 may be programmed such that each first responder starts with a base score (for example, twenty points). As indicated in FIG. 6, in some embodiments, the first electronic processor 205 either adds to or subtracts from the base score depending on the characteristics of the first responder. For example, when the first electronic processor 205 determines that the first responder possesses a gun, the first electronic processor 205 may add twenty points to the score of the first responder. In some embodiments, when the first electronic processor 205 receives information from the public safety database 320 indicating that the first responder has a high skill level in hand-to-hand combat (for example, the first responder has a black belt in a martial art), the first electronic processor 205 adds ten points to the score of the first responder. On the other hand, when the first electronic processor 205 determines that the first responder is injured, the first electronic processor 205 may subtract ten points from the score of the first responder.

At block 415, the first electronic processor 205 identifies the suspect at an incident area. For example, the first electronic processor 205 may use the video analytics engine to perform facial recognition of the suspect using image data received from at least one of the first camera 120 and the second camera 220. In some embodiments, the first electronic processor 205 receives an input from the first responder on the display 230 that at least partially identifies the suspect, for example, when the first responder recognizes the suspect, the first responder may provide the name of the suspect to the first electronic processor 205 via the display 230. Alternatively, when the first responder does not recognize the suspect, the first responder may provide descriptive information about the suspect (for example, sex, hair color, approximate height and weight, and the like) to the first electronic processor 205 via input components of a graphical user interface presented on the display 230. The first electronic processor 205 may use the descriptive information when identifying the suspect through facial recognition (for example, to confirm that the suspect identified corresponds to the descriptive information provided by the first responder).

At block 420, the first electronic processor 205 identifies a second plurality of characteristics of the suspect similar to the identification of the first plurality of characteristics of the first responder. In some embodiments, many of the second plurality of characteristics are the same as the first plurality of characteristics. For example, the first electronic processor 205 may identity the second plurality of characteristics to be offensive characteristics, defensive characteristics, speed characteristics, and experience characteristics as described previously herein with respect to the first responder. However, the experience characteristics of the suspect may instead include, but are not limited to, a number of prior arrests or charges that the suspect has in his or her criminal record and whether the suspect is on parole. In some embodiments, the second plurality of characteristics may also include the likelihood that the suspect is an extremist, a drug user, and the like. Such likelihoods may be determined using social media information from the second server 115 as described hereinafter.

Figure 5B:
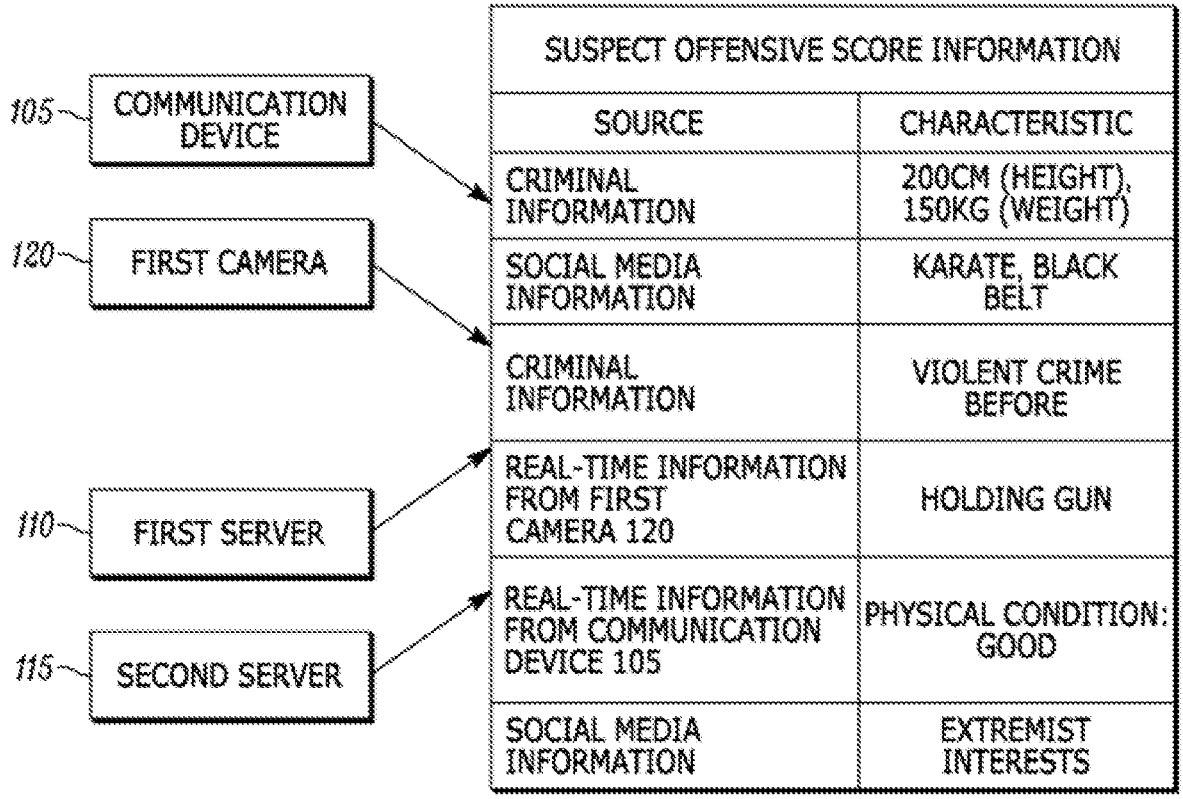
FIG. 5B is a block diagram that illustrates an exemplary table of a second plurality of characteristics of a suspect.

At block 425, the first electronic processor 205 generates a second score for the suspect based on the second plurality of characteristics of the suspect. In some embodiments, many of the second plurality of characteristics are determined in the same manner as the first plurality of characteristics was determined. FIG. 5B is a block diagram that illustrates an exemplary table of the second plurality of characteristics determined by the first electronic processor 205. As shown in FIG. 5B, the first electronic processor 205 may generate the table of the second plurality of characteristics based on at least one of real-time information from the communication device 105 (for example, at least one of image data from the second camera 220 and information entered by a public safety officer on the display 230), real-time information from other sources (for example, image from the first camera 120), criminal information from the first server 110, and social media information from the second server 115.

In some embodiments, the first electronic processor 205 determines a score for each of the second plurality of characteristics based on at least one of criminal information from the public safety database 320 (in other words, based on criminal records) and image data from at least one of the first camera 120 and the second camera 220 for example, in some embodiments, the first electronic processor 205 uses the video analytics engine to determine one or more characteristics of the suspect upon receiving image data from the second camera 220. For example, in some embodiments, the video analytics engine determines whether the suspect is in possession of a weapon or whether the suspect is injured, in some embodiments, the first electronic processor 205 also sends a request via the first network interface 215 to the second server 115 to receive social media information from the second server 115. Upon receiving the social media information via the first network interface 215 from the second server 115, the first electronic processor 205 may use a social media analytics engine to determine one or more characteristics of the suspect. For example, in some embodiments, the social media analytics engine determines the likelihood that the suspect is an extremist, a drug user, and the like based on the social media information described previously herein.

The first electronic processor 205 then generates the second score based on the characteristics of the suspect in a similar manner as explained previously herein with respect to the first score of the first responder. FIG. 6 illustrates an exemplary table that shows how the first electronic processor 205 may generate scores based on characteristics. In some embodiments, the first electronic processor 205 is programmed such that each suspect starts with a base score (for example, twenty points). As indicated in FIG. 6, the first electronic processor 205 then either adds to or subtracts from the base score depending on the characteristics of the suspect in a similar manner as described previously herein with respect to the first score of the first responder. For example, in some embodiments, when the first electronic processor 205 receives criminal information from the public safety database 320 indicating that the suspect has a propensity for violence (for example, based on a history of violent crimes in the criminal record of the suspect), the first electronic processor 205 adds ten points to the score of the suspect. In some embodiments, when the first electronic processor 205 receives social media information from the second server 115 indicating that the suspect has a propensity for extremism or violence (for example, a social media account of the suspect includes violent or extreme comments or photographs), the first electronic processor 205 adds ten points to the score of the suspect.

The above description of generating the first score and the second score is exemplary. In some embodiments, the first electronic processor 205 identifies additional characteristics or a different combination of the characteristics mentioned previously herein. In some embodiments, the base score of the first responder and the suspect is different (for example, depending on age or experience of the first responder or depending on the criminal record of the suspect). In some embodiments, the first electronic processor 205 adds or subtracts a different number of points than stated previously herein depending on the characteristics of the first responder and the suspect, in some embodiments, the first score and the second score are non-numerical. For example, in some embodiments, the first score and the second score are ratings represented by a color or a letter. In such embodiments, when the first score or the second score is above one hundred points, for example, the first electronic processor 205 determines that the respective score is green or is an "A." On the other hand, when the first score or the second score is less than thirty points, for example, the first electronic processor 205 may determine that the respective score is red or is a "D."

At block 130, the first electronic processor 205 compares the first score for the first responder and the second score for the suspect. FIGS. 7A and 7B illustrate tables of exemplary scores for a public safety officer and a suspect, respectively. As shown in FIGS. 7A and 7B, each of the public safety officer and the suspect had a base score of twenty points. However, based on their respective characteristics, the public safety officer has a total score of forty-four (see FIG. 7A) and the suspect has a total score of seventy-three (see FIG. 7B). In some embodiments, the first electronic processor 205 determines whether the first score is higher than the second score. In some embodiments, the first electronic processor 205 determines a difference between the first score and the second score. At block 435, the first electronic processor 205 sends an electrical signal to an output device (for example, the speaker 225, the display 230, and the like) to control the output device to output a recommended action based on the comparison of the first score and the second score (for example, see FIG. 2C). While FIG. 2C shows the recommended action in the form of text on the display 230, in some embodiments, the communication device 105 may notify a user of the recommended action in other ways. For example the communication device 105 may flash a light (for example, a light emitting diode), illuminate a light a predetermined color, provide an audible recommended action using the speaker 225, or provide a haptic notification of the recommended action. In some embodiments, the first electronic processor 205 controls the display 230 to display the first score and the second score. In such embodiments, the display 230 may display a numerical representation of the first score and the second score. In some embodiments, the display 230 may display the first score and the second score as ratings represented by a color or a letter as explained previously herein. In some embodiments, the display 230 may also display the respective characteristics of the public safety officer and the suspect that were used to determine the first score and the second score. For example, the display 230 may display tables similar to the tables shown in FIGS. 7A and 7B.

In some embodiments, the recommended action is an aggressive action (for example, arrest the suspect), a defensive action (for example, retreat from the suspect), or a moderate action (for example monitor the suspect). For example, when the first score is higher than the second score and the difference between the first score and the second score exceeds a predetermined threshold (for example, thirty points), the first electronic processor 205 controls the output device to recommend that the first responder engage the suspect (in other words, approach and confront the suspect). In tins example, the first electronic processor 205 determines that the first responder has an advantage over the suspect. As another example, when the second score is higher than the first score (see, for example, FIGS. 7A and 8B) the first electronic processor 205 controls the output device to recommend that the first responder does not engage the suspect and instead waits for additional assistance (for example, see the recommendation on the display 230 of FIG. 2C). In this second example, the first electronic processor 205 determines that the suspect has an advantage over the first responder or that the advantage of the first responder over the suspect is not above the predetermined threshold. In some embodiments, the output device outputs at least one of a visual message on the display 230, an audible message via the speaker 225, and a haptic notification using another output device.

Figure 8:
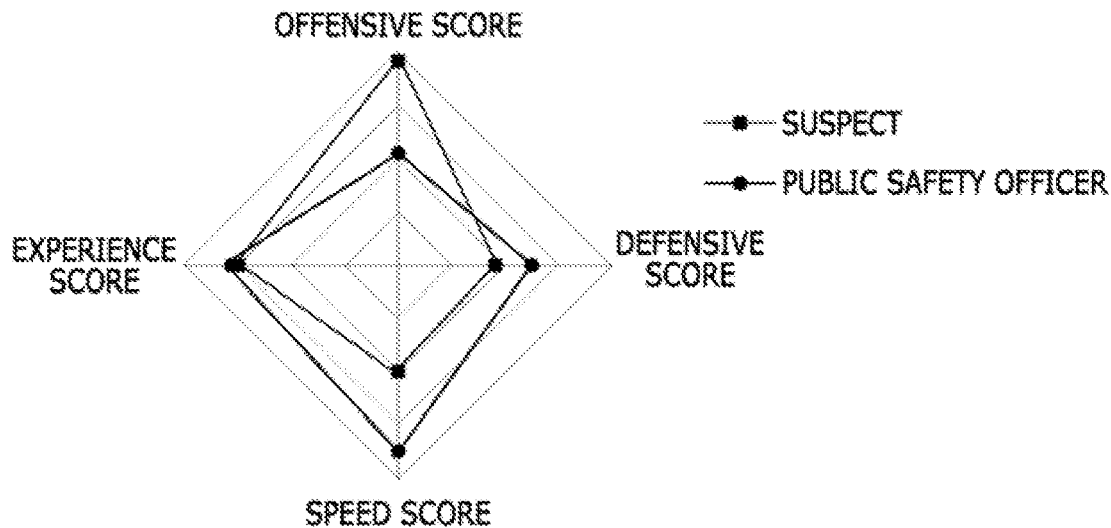
FIG. 8 is an exemplary chart that may be displayed on a display of the communication device of FIG. 2 that illustrates a first score and a second score for each of a category of characteristics of the first responder and the suspect.

In some embodiments, the first electronic processor 205 generates a first and second score for each of a category of characteristics (for example, offensive, defensive, speed, and experience) for each of the first responder and the suspect. In such embodiments, the first electronic processor 205 generates the first score and the second score for each of the categories of characteristics in a similar manner as described previously herein with respect to generation of a single first score and a single second score. For example, the first electronic processor 205 may generate the first and the second score for the category of offensive characteristics by adding and subtracting points to and from a base offensive score based on the characteristics of the first responder and the suspect, respectively. In some embodiments, the first electronic processor 205 compares the first score and the second score for each of the categories of characteristics. FIG. 8 illustrates an exemplary chart that may be displayed on the display 230 to convey the results of such comparisons to the public safety officer. In the exemplary chart of FIG. 8, the intersection of each diamond on each axis represents increments of twenty points. For example, in FIG. 8, the offensive score of the suspect is near eighty points and the offensive score of the public safety officer is near forty points. As shown in FIG. 8, the first score and the second score for each of the categories of characteristics are graphically illustrated to indicate the advantages and disadvantages that the public safety officer has with respect to the suspect. For example, in FIG. 8, the public safety officer has a lower score than the suspect with respect to offensive characteristics. However, the public safety officer has a higher score than the suspect with respect to speed characteristics. In some embodiments, the display 230 may display the first score and the second score for each of the categories of characteristics in a table or list format.

In some embodiments, the first electronic processor 205 compares the scores of each of the category of characteristics to determine the recommended action output by the output device, for example, as shown in FIG. 8, when the first responder has a lower offensive score than the suspect and a higher speed score than the suspect, the first electronic processor 205 controls the output device to recommend that the first responder follow and monitor the suspect until additional public safety officers arrive. As another example, when the firm responder has a significantly lower score in all categories (in other words, a difference between the scores exceeds a predetermined threshold), the first electronic processor 205 controls the output device to recommend that the first responder retreat until additional public safety officers arrive.

Although the above description of the method 400 refers to a single first responder and a single suspect, in some embodiments, the first electronic processor 205 evaluates the characteristics of more than one first responder. Similarly, in some embodiments, the first electronic processor 205 identifies more than one suspect and evaluates the characteristics of more than one suspect. In such embodiments, the first electronic processor 205 adds the scores of the first responders located within a predetermined distance from each other to generate a combined first score. In such embodiments, the first electronic processor 205 also adds the scores of the suspects located within a predetermined distance from each other to generate a combined second score. The first electronic processor 205 then compares the combined first score and the combined second score and control the output device to output a recommended action based on the comparison. When outputting the recommended action, the first electronic processor 205 may list the public safety officers that were accounted for its the first score and send the recommended action to the communication devices of such public safety officers. For example, the first electronic processor 205 sends the recommended action via the first network interface 215 to other communication devices of public safety officers located nearby.

In some embodiments, when determining the first score for the first responders, one or more communication devices include a geographic coordinate sensor that may be used to determine that other communication devices are located within a predetermined distance. In some embodiments, the communication devices of each of the first responders located within a predetermined distance from the communication device 105 send identification information to the communication device 105 performing the method 400. The communication device 105 may then request public safety information from the first server 110 as described previously herein. Alternatively, in some embodiments, each of the communication devices located within a predetermined distance front each other send requests to the first server 110 to provide public safety information to the communication device 105 performing the method 400. Alternatively, each communication device may perform the method 400, and communication devices located within a predetermined distance from each other may provide scores to each other. Each communication device may then add the scores together to generate the combined first score. In some embodiments, nearby communication devices similarly communicate the second plurality of characteristics of the suspects and determine the combined second score of the suspects.

In some embodiments, when the first electronic processor 205 determines that the first score of the first responder is less than the predetermined threshold above the second score of the suspect, the first electronic processor 205 transmits a request for back-up via the first network interface 215 to at least one other communication device located nearby. In some embodiments, the request for back-up is transmitted through the network 125. In some embodiments, the request for back-up is transmitted over an ad-hoc network including a plurality of communication devices. In some embodiments, the request for back-up includes an amount of back-up required (in other words, a score required) to increase the first score above the predetermined threshold compared to the second score. For example, when the first electronic processor 205 determines that the first score is near the predetermined threshold above the second score (in other words, the public safety officer has an advantage over the suspect, but the advantage is not high enough to recommend engaging the suspect), the request for back-up may indicate that one additional public safety officer with average physical condition is needed to recommend engaging the suspect. As another example, when the first electronic processor 205 determines that the first score is lower than the second score (in other words, the suspect has an advantage over the public safety officer), the request for back-up may indicate that two or more public safety officers with guns are needed to recommend engaging the suspect.

In some embodiments, when the first electronic processor 205 determines that the first score of the first responder is less than the predetermined threshold above the second score of the suspect, the first electronic processor 205 transmits a recommendation to a communication device or other device located at a command center. In such embodiments, the recommendation may include a suggested amount of additional assistance required at the incident area to increase the first score above the predetermined threshold above the second score. Public safety officers at the command center may then instruct other public safety officers to travel to the incident area to provide additional assistance.

In some embodiments, when the first score is less than the predetermined threshold above the second score, the first electronic processor 205 identifies at least one additional nearby communication device associated with a public safety officer that has a third score that, when added to the first score, amounts to a combined score greater than the predetermined threshold above the second score. For example, the first electronic processor 205 requests characteristics of public safety officers or scores of public safety officers located within a predetermined distance from the communication device 205 or located nearest to the communication device 105. The first electronic processor 205 then determines or receives a third score for at least one additional public safety officer located nearby the communication device 105. The first electronic processor 205 then controls the display 230 to output a list of the at least one additional public safety officers that have a third score that, when added to the first score to generate a combined score, is sufficient to exceed the predetermined threshold above the second score. The first responder may then communicate with one of the other public safety officers on the list to request back-up. As mentioned previously herein, in some embodiments, communication between communication devices occurs, among other ways, over the network 125 and over an ad-hoc network including a plurality of communication devices.

As described previously herein, the method 400 of providing decision support to first responders is executed by the first electronic processor 205 of the communication device 105. In some embodiments, the method 400 executed by other devices including, but not limited to, the first server 110 and other communication devices or computers (for example, located in a public safety vehicle or at a public safety command center). In such embodiments, the device executing the method communicates with the communication device 105 to receive information and to transmit a recommended action to the communication device 105.

Figure 9:
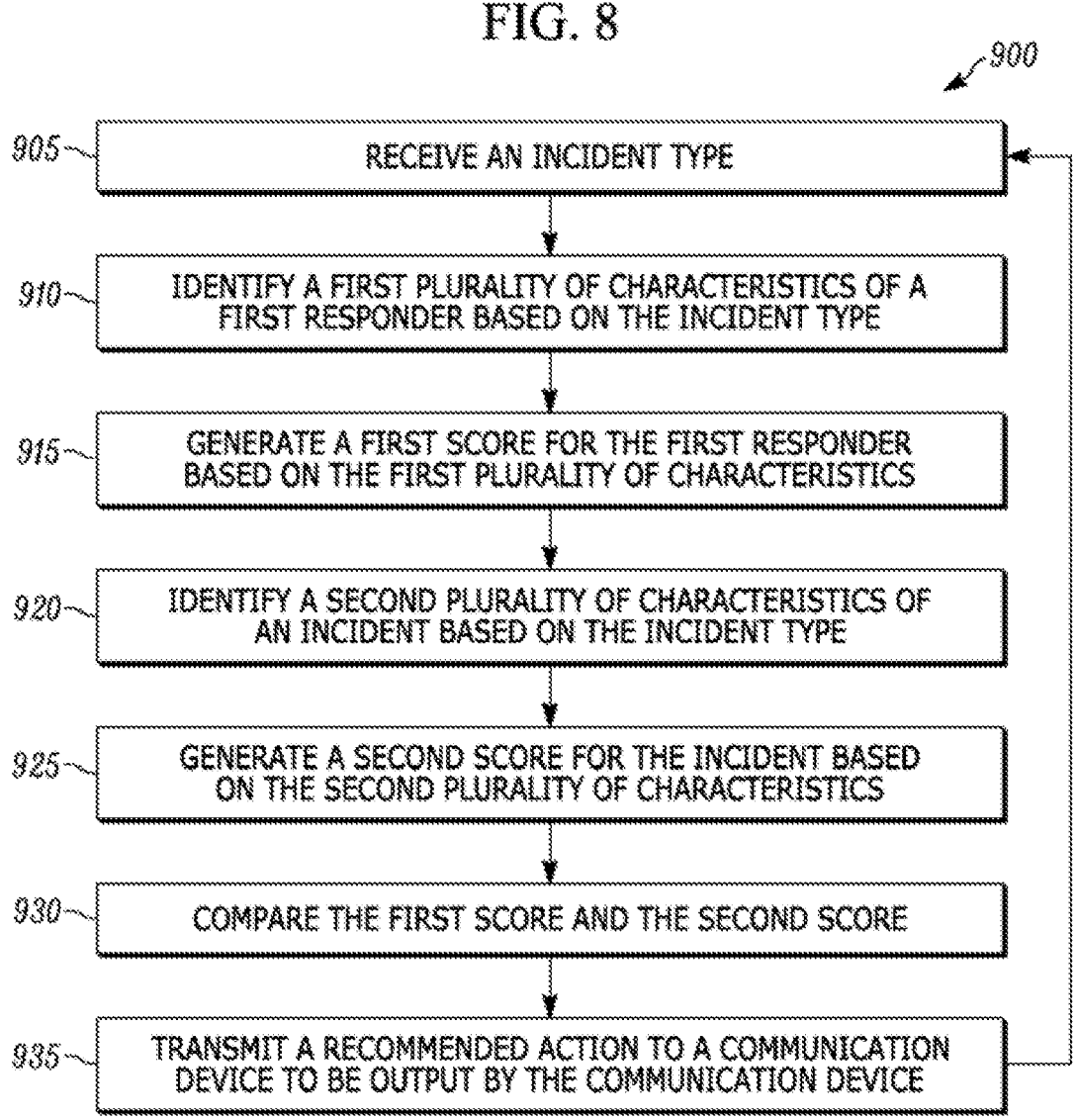
FIG. 9 is a flowchart of another method of providing decision support to first responders performed by the first server of FIG. 3 according to one exemplary embodiment.

For example, FIG. 9 illustrates a method 900 of providing decision support to first respondent that is performed by the second electronic processor 305 of the first server 110. At block 905, the second electronic processor 305 receives, via the second network interface 315, an incident type of an incident from the communication device 105. The first electronic processor 205 of the communication device 105 receives an electrical signal front the display 230 that indicates the incident type of the incident as selected by a user of the communication device 105. The first electronic processor 205 controls the display 230 to display a list of incident types for the public safety officer to choose from (for example, see FIG. 2B). In some embodiments, the incident types include, but are not limited to, a fire, an explosion, providing paramedic aid, and suspect searching (as described previously herein with respect to the method 400). When the public safety officer selects the incident type on the display 230, the communication device 105 then transmits the incident type over the network 125 to the first server 110.

In some embodiments, the type of incident selected by public safety officers may be different even when the public safety officers are handling the same incident. For example, when the incident is an explosion, a paramedic may select that the incident involves providing paramedic aid and a police officer may select that the incident is an explosion. In this example, the selection of the type of incident depends on the task of the public safety officer. For example, the task of the paramedic is to provide paramedic aid to injured victims while the task of the police officer may be to determine whether there are any other explosive devices or other potential hazards at the incident area.

At block 910, the second electronic processor 305 identifies a first plurality of characteristics of the first responder based on the incident type. For example, when the incident type is suspect searching, the first plurality of characteristics may be the characteristics described previously herein with respect to block 405 of FIG. 4. In some embodiments, when the incident type is a fire, the first plurality of characteristics is equipment characteristics related to the type of fire and experience characteristics of the first responder with respect to the type of fire. In some embodiments, the equipment characteristics include, but are not limited to, a number and type of fire trucks at the incident area, a supply of water accessible at or near the incident area, an amount of protective gear available at the incident area to be used by the first responder, and an ability to communicate with other first responders or other public safety personnel (for example, located at a command center). In some embodiments, the experience characteristics include, but are not limited to, a number of years that the first responder has been a public safety officer and a number of fires that the first responder has experienced that are similar to the present fire for example, when the fire is a wild fire, the second electronic processor 305 identifies certain equipment and experience as relevant characteristics of the first responder. As another example, when the fire is a house fire, the second electronic processor 305 identifies different equipment and experience as relevant characteristics of the first responder. Similarly, when the fire is a chemical fire, the second electronic processor 305 identifies other equipment and experience as relevant characteristics of the first responder. In some embodiments, the first plurality of characteristics also includes a number of first responded present at the incident area.

As another example, when the incident type involves providing paramedic aid, the first plurality of characteristics includes, but is not limited to, equipment characteristics and experience characteristics of the first responder. In some embodiments, the equipment characteristics include a number of ambulances, an amount and type of medical equipment at the incident area, and an ability to communicate with other first responders or other public safety personnel (for example, located at a command center). In some embodiments, the equipment characteristics include an amount of protective gear available at the incident area to be used by the first responder (for example, when potentially toxic chemicals may be present at the incident area). In some embodiments, the experience characteristics include a number of years that the first responder has been a public safety officer and a number of paramedic aid situations that the first responder has experienced that are similar to the present situation. In some embodiments, the first plurality of characteristics also includes a number of first responders present at the incident area.

As another example, when the incident type is an explosion, the first plurality of characteristics includes, but is not limited to, equipment characteristics and experience characteristics of the first responder. In some embodiments, the equipment characteristics include devices or animals at the incident area that are capable of detecting an explosive device, an amount of protective gear available at the incident area to be used by the first responder, and an ability to communicate with other first responders or other public safety personnel (for example, located at a command center). In some embodiments, the experience characteristics include a number of years that the first responder has been a public safety officer and a number of explosion situations that the first responder has experienced that are similar to the present situation. In some embodiments, the first plurality of characteristics also includes a number of first responders present at the incident area.

At block 915, the second electronic processor 305 generates a first score for the first responder based on the first plurality of characteristics. The second electronic processor 505 may generate the first score in a similar manner as described previously herein with respect to block 410 of FIG. 4. For example, in some embodiments the second electronic processor 305 requests one or more characteristics of the first responder from the public safety database 320 (for example, previous experience with similar incidents, type of training or certification received by the first responder, and the like).

In some embodiments, the second electronic processor 305 also determines one or more characteristics of the first responder by receiving data from the personal area network sensor 235 that is transmitted to the first server 110. For example, the personal area network sensor 235 may determine what equipment is nearby the communication device 105 and transmit this information to the first server 110. Alternatively, in some embodiments, the equipment nearby the communication device 105 (for example, fire trucks, ambulances, protective gear, and the like) includes a device configured to communicate to the first server 110. In such embodiments, the second electronic processor 505 determines that the equipment is located near the communication device 105 based on communication with the equipment and with the communication device 105. The second electronic processor 305 also sends a request via the second network interlace 315 to the first camera 102, the second camera 220, or another camera to receive image data from the first camera 120, the second camera 220, or another camera. Upon receiving the image data via the second network interface 315, the second electronic processor 305 uses a video analytics engine to determine one or more characteristics of the first responder. For example, in some embodiments, the video analytics engine determines the equipment nearby the first responder or whether the first responder is injured.

After determining the characteristics of the first responder, the second electronic processor 305 then generates the first score based on the characteristics of the first responder as explained previously herein with respect to block 410 of FIG. 4 (for example, adding to or subtracting from a base score of the first responder based on the characteristics of the first responder). For example, when the incident is a fire, the second electronic processor 305 may add twenty points to the base score of the first responder for each fire truck that is present at the incident area. In some embodiments, when the incident is a fire, the second electronic processor 305 subtracts twenty points from the base score of the first responder when an amount of water accessible nearby the fire is below a predetermined threshold. In some embodiments, when the incident involves providing paramedic aid, the second electronic processor 305 adds ten points for each ambulance present at the incident area. In some embodiments, when the incident is an explosion, the second electronic processor 305 adds ten points for each device or animal at the incident area that is capable of detecting an explosive device.

At block 920, the second electronic processor 305 identifies a second plurality of characteristics of the incident based on the incident type. For example, when the incident type is a fire, the second plurality of characteristics includes a type of fire, weather at the incident area, environment surrounding the incident area, a size of the fire, a hazardous material rating at the incident area, construction characteristics of the structure at the incident area, and the likelihood that people are located in the incident area.

In some embodiments, when the fire is a wild fire the second electronic processor 305 identifies certain characteristics as relevant characteristics of the incident. For example, the weather and environment surrounding the fire may be relevant characteristics identified by the second electronic processor 305 (in other words, characteristics relevant to the ability of the wild fire to spread). In some embodiments, when the fire is a house fire, the second electronic processor 305 identifies different characteristics as relevant characteristics of the incident. For example, the size of the fire and the construction characteristics of the house may be relevant characteristics identified by the second electronic processor 305. Similarly, when the fire is a chemical fire, the second electronic processor 305 identifies further characteristics as relevant characteristics of the incident. For example, the hazardous material rating of the chemical (in other words, flammability, toxicity, and the like) may be a relevant characteristic identified by the second electronic processor 305.

As another example, when the incident type involves providing paramedic aid, the second plurality of characteristics may include, but are not limited to, a number of victims injured, a terrain of the incident area, whether there is a threat of danger from a person at the incident area (for example, whether a person at the incident area is moving and holding a weapon), and whether there is a threat of danger from the environment of the incident area (for example, whether part of building may collapse onto fire incident area).

As another example, when the incident type is an explosion, the second plurality of characteristics may be similar to those described previously herein with respect to the incident involving, providing paramedic aid. In some embodiments, the second plurality of characteristics may also include whether there are objects present that are potentially explosive (for example, a propane tank or a package that may contain a bomb) and whether there are potentially dangerous chemicals present at the incident area (for example, flammable or toxic chemicals).

At block 925, the second electronic processor 305 generates a second score for the incident based on the second plurality of characteristics. The second electronic processor 305 may generate the second score in a similar manner as described previously herein with respect to block 410 of FIG. 4. In some embodiments, the second electronic processor 305 requests location information from a third server. In some embodiments, the second electronic processor 305 determines the type of fire based on the location of the communication device 105 (for example, using the geographic coordinates of the communication device 105). In other words, the second electronic processor 305 determines whether the geographic coordinates of the communication device 105 indicate that the incident is occurring in a city, in a neighborhood, at a farm, and the like. Alternatively, in some embodiments, the communication device 105 transmits the type of fire to the first server 110 in response to a public safety officer entering the type of fire on the display 230.

In some embodiments, the second electronic processor 305 sends a request via the second network interface 315 to the first camera 120, the second camera 220, or another camera to receive image data from the first camera 120, the second camera 220, or another camera. Upon receiving the image data via the second network interface 315 the second electronic processor 305 may use the video analytics engine to determine one or more characteristics of the incident. For example, in some embodiments, the video analytics engine determines a size of a fire, a number of victims injured, a terrain of the incident area, whether there is a threat of danger from a person at the incident area, and whether there is a threat of danger from the environment of the incident area, among other characteristics.

After determining the characteristics of the incident, the second electronic processor 305 then generates the second score based on the characteristics of the incident as explained previously herein with respect to block 410 of FIG. 4 (for example, adding to or subtracting from a base score of the incident based on the characteristics of the incident). For example, when the incident is a fire, the second electronic processor 305 may add twenty points to the base score of the incident when the weather is windy and the environment surrounding the fire is dry. In some embodiments, when the incident is a fire, the second electronic processor 305 adds ten points to the score of the incident when the size of the fire exceeds a predetermined threshold (for example, flames larger than ten feet). In some embodiments, when the incident involves providing paramedic aid the second electronic processor 305 adds twenty points when there is a threat of danger at the incident area. In some embodiments, when the incident is an explosion, the second electronic processor 305 adds twenty points when there is a potentially explosive object at the incident area.

At block 930, the second electronic processor 305 compares the first score for the first responder and the second score for the incident in a similar manner as described previously herein with respect to block 430 of FIG. 4. At block 935, the second electronic processor 305 transmits a recommended action to the communication device 105 to be output by the communication device 105 as described previously herein with respect to block 435 of FIG. 4. For example, when the incident is a fire, the recommended action includes containing the fire, adjusting position (for example, based on the direction of wind at the incident), and waiting for additional assistance. When the incident involves providing paramedic aid, the recommended action may include, but is not limited to, providing aid to victims, transporting a victim to a hospital, and waiting to provide aid until a threat of danger has been eliminated or until more medical equipment is available. When the incident is an explosion, the recommended action may include, but is not limited to, evacuating people, from the incident area, sweeping the incident area with devices or animals capable of detecting explosive devices, and waiting to enter the incident area until at least one of additional assistance arrives, additional equipment arrives, and a threat of danger has been eliminated.

In some embodiments, when the second electronic processor 305 determines that the communication device 105 is unable to communicate with other first responders or other public safety personnel (for example, at a command center), the recommended action may include retreating from the incident area until such communication is available. Such a recommendation may occur during any type of incident.

While the method 900 is described previously herein as being executed by the second electronic processor 305 of the first server 110, in some embodiments, the method 900 is executed by other devices including, but not limited to, the communication device 105 and other communication devices or computers (for example, located in a public safety vehicle or at a public safety command center).

Similar to the method 400 of FIG. 4, the above description of generating the first score and the second score is exemplary. In other embodiments, the second electronic processor 305 identifies additional characteristics or a different combination of the characteristics mentioned previously herein. In some embodiments, the base score of the first responder and the incident is different (for example, depending on age or experience of the first responder or depending on the type of incident). For example, in some embodiments, a fire has a base score of fifty while a paramedic aid incident may have a base score of twenty-five. In some embodiments, the second electronic processor 305 adds or subtracts a different number of points than stated previously herein depending on the characteristics of the first responder and the incident.

Also similar to the method 400 of FIG. 4, although the above description of the method 900 refers to a single first responder, in some embodiments, the second electronic processor 305 evaluates the characteristics of more than one first responder in a similar manner as described previously herein with respect to the method 400. Also in a similar manner as described above with respect to the method 400, in some embodiments, after executing the method 900, the second electronic processor 305 transmits a request for back-up or identifies at least one additional communication device associated with a public safety officer that has a third score that, when added to the first score, amounts to a combined score greater than the predetermined threshold above the second score.

As indicated in FIGS. 4 and 9, in some embodiments, the methods 400 and 900 repeat to dynamically provide decision support to first responders as at least one of the characteristics of the first responder, the suspect, and the incident change, for example, as the method 400 or the method 900 repeats, the video analytics engine of the electronic processor 205/305 may recognize that the first responder has been injured and may subtract points from the first score of the first responder such that the recommended action changes from an original recommended action. In some embodiments, the methods 400 and 900 do not repeat unless at least one of the characteristics of the first responded the suspect, and the incident has changed. For example, when the electronic processor 205/305 determines that at least one of the characteristics of the first responder, the suspect, and the incident has changed, the electronic processor 205/305 repeats the respective method 400 and 900 to regenerate the first score, the second score, and the recommended action.

When comparing the first score and the second score (at block 430 of FIG. 4 and at block 930 of FIG. 9), in some embodiments, the electronic processor 205/305 uses historical data of previous similar incidents and outcomes to determine the recommended action provided by the communication device 105. For example, before outputting a recommended action on the communication device 105, the electronic processor 205/305 may compare the first score and the second score to corresponding scores of previous incidents of the same incident type. Such historical data may be stored on the first server 110 along with an outcome of the previous incident (for example, whether the outcome of the recommended action was positive, negative, or neutral). In some embodiments, the recommended actions stored from previous incidents are scored based on the outcome of the previous incident, for example, when the recommended action was to engage the suspect and the public safety officer successfully engaged the suspect, the stored recommended action may foe given a score of twenty points. As another example, when the recommended action was not successful, the stored recommended action may be given a score of negative twenty points.

In some embodiments, the electronic processor 205/305 uses the historical data along with the comparison of the first score and the second score to output a recommended action. For example, the electronic processor 205/305 determines how similar the current incident is to a previous incident by comparing at least one of the incident type, the first plurality of characteristics, the second plurality of characteristics, the first score, and the second, of the score of the two incidents. When the similarities exceed a predetermined threshold, the electronic processor 205/305 adjusts the first score and the second score of the current incident based on the historical data as explained above. Alternatively, in some embodiments, when the similarities between the first score and the second score of the two incidents exceed a second predetermined threshold (for example, when the incidents are very similar to each other), the electronic processor 205/305 outputs a recommended action based solely on the historical data.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any elements) that may cause any benefit, advantage, or solution to occur or become more pronounced are not to be construed as a critical, required, or essential features or elements of any or ail the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has," "having," "includes," "including," "contains," "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a," "has . . . a," "includes . . . a," or "contains . . . a" does not, without more constraints, preclude the existence of additional identical elements in the process, method, article, or apparatus that comprises, has, includes, contains the element. The terms "a" and "an" are defined as vine or more unless explicitly stated otherwise herein. The terms "substantially," "essentially," "approximately," "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (of "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure, it is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

We claim:

1. A method of providing decision support to first responders, the method comprising:
   identifying, with an electronic processor, a first plurality of characteristics of a first responder;
   generating, with the electronic processor, a first score for the first responder based on the first plurality of characteristics;
   receiving, with the electronic processor, image data of an incident area from a camera,
   identifying, with a video analytics engine of the electronic processor, a suspect at the incident area using facial recognition of the image data;
   identifying, with the electronic processor, a second plurality of characteristics of the suspect, wherein the video analytics engine determines at least one of the second plurality of characteristics based on the image data;
   generating, with the electronic processor, a second score for the suspect based on the second plurality of characteristics;
   comparing, with the electronic processor, the first score and the second score; and
   outputting, with an output device electrically connected to the electronic processor, a recommended action based on the comparison of the first score and the second score,
      wherein the comparison indicates that the first score is at least one of the group consisting of (i) less than the second score and (ii) less than a predetermined threshold above the second score, and
      wherein the recommended action indicates that the first responder should not engage the suspect and should wait for additional assistance; and
   in response to the comparison indicating that the first score is at least one of the group consisting of (i) less than the second score and (ii) less than the predetermined threshold above the second score, transmitting, with a network interface, a request for back-up to at least one communication device, the request for back-up including an amount of back-up required to increase the first score above the predetermined threshold compared to the second score.

2. The method of claim 1, further comprising:
receiving, with the electronic processor via a network interface, public safety information of the first responder from a database;
determining, with the electronic processor, at least one of the first plurality of characteristics based on the public safety information;
receiving, with the electronic processor via the network interface, criminal information of the suspect from the database; and
determining, with the electronic processor, at least one of the second plurality of characteristics based on the criminal information.

3. The method of claim 1, further comprising:
transmitting, with a network interface, a request for social media information of the suspect;
receiving, with the network interface, the social media information of the suspect;
determining, with the electronic processor, at least one of the second plurality of characteristics based on the social media information.

4. The method of claim 1, wherein identifying, with the electronic processor, the first plurality of characteristics and the second plurality of characteristics includes identifying, with the electronic processor, at least one of the group consisting of offensive characteristics, defensive characteristics, speed characteristics, and experience characteristics.

5. The method of claim 1, wherein identifying, with the electronic processor, the first plurality of characteristics of the first responder includes identifying, with the electronic processor, at least one of the group consisting of a height of the first responder, a weight of the first responder, a physical condition of the first responder, a skill level of the first responder, an experience level of the first responder, and whether the first responder is in possession of a weapon.

6. The method of claim 1, wherein identifying, with the electronic processor, the second plurality of characteristics of the suspect includes identifying, with the electronic processor, at least one of the group consisting of a height of the suspect, a weight of the suspect, a physical condition of the suspect, a skill level of the suspect, a propensity for violence of the suspect, a propensity for extremism of the suspect, and whether the suspect is in possession of a weapon.

7. The method of claim 1, wherein outputting the recommended action includes at least one of the group consisting of outputting a visual message on a display, producing an audible message via a speaker, and producing a haptic notification.

8. The method of claim 1, wherein transmitting the request for back-up to the at least one communication device occurs over an ad-hoc network including a plurality of communication devices.

9. The method of claim 1, further comprising:
in response to the comparison indicating that the first score is at least one of the group consisting of (i) less than the second score and (ii) less than the predetermined threshold above the second score,
identifying, with the electronic processor, a third plurality of characteristics of a public safety officer,
generating, with the electronic processor, a third score for the public safety officer based on the third plurality of characteristics,
determining, with the electronic processor, that a combined score including a sum of the first score and the third score is greater than the predetermined threshold above the second score, and
in response to determining that the combined score is greater than the predetermined threshold above the second score, displaying, on a display, a list including the public safety officer.

10. A communication device comprising:
a memory;
a network interface;
an output device;
a display; and
an electronic processor configured to
identify a first plurality of characteristics of a first responder,
generate a first score for the first responder based on the first plurality of characteristics,
identify a suspect at an incident area,
identify a second plurality of characteristics of the suspect,
generate a second score for the suspect based on the second plurality of characteristics,
compare the first score and the second score, and
transmit an electrical signal to the output device in response to comparing the first score and the second score;
wherein the output device outputs a recommended action based on the electrical signal, the recommended action being based on the comparison of the first score and the second score,
wherein the comparison indicates that the first score is at least one of the group consisting of (i) less than the second score and (ii) less than a predetermined threshold above the second score, and
wherein the recommended action indicates that the first responder should not engage the suspect and should wait for additional assistance;
wherein the electronic processor includes a video analytics engine configured to determine at least one of the group consisting of the first plurality of characteristics and the second plurality of characteristics based on image data received from at least one of a first camera and a second camera; and
wherein in response to the comparison indicating that the first score is at least one of the group consisting of (i) less than the second score and (ii) less than the predetermined threshold above the second score, the electronic processor is further configured to transmit, with the network interface, a request for back-up to at least one communication device, the request for back-up including an amount of back-up required to increase the first score above the predetermined threshold compared to the second score.

11. A method of providing decision support to first responders, the method comprising:
receiving, with a network interface, an incident type from a communication device, the incident type having been selected on a display of the communication device;
receiving, with an electronic processor, image data of an incident area from a camera;
identifying, with the electronic processor and based on the incident type, a first plurality of characteristics of a first responder;

generating, with the electronic processor, a first score for the first responder based on the first plurality of characteristics;

identifying, with the electronic processor and based on the incident type, a second plurality of characteristics of an incident;

generating, with the electronic processor, a second score for the incident based on the second plurality of characteristics;

comparing, with the electronic processor, the first score and the second score;

transmitting, with the network interface, a recommended action to the communication device, the recommended action being output by an output device of the communication device and being based on the comparison of the first score and the second score, wherein the comparison indicates that the first score is at least one of the group consisting of (i) less than the second score and (ii) less than a predetermined threshold above the second score, and wherein the recommended action indicates that the first responder should wait for additional assistance; and in response to the comparison indicating that the first score is at least one of the group consisting of (i) less than the second score and (ii) less than the predetermined threshold above the second score, transmitting, with the network interface, a request for back-up to at least one other communication device, the request for back-up including an amount of back-up required to increase the first score above the predetermined threshold compared to the second score;

wherein identifying at least one of the first plurality of characteristics or the second plurality of characteristics includes determining, with a video analytics engine of the electronic processor, the at least one of the group consisting of the first plurality of characteristics and the second plurality of characteristics based on the image data received from the camera.

12. The method of claim 11, further comprising:

retrieving, with the electronic processor, public safety information of the first responder from a database; and determining, with the electronic processor, at least one of the first plurality of characteristics based on the public safety information.

13. The method of claim 11, wherein identifying the first plurality of characteristics of the first responder includes identifying, with the electronic processor and based on the incident type, at least one of the group consisting of a physical condition of the first responder, a skill level of the first responder, an experience level of the first responder, an amount and a type of equipment at the incident area, a supply of water accessible at the incident area, and an amount of protective gear available at the incident area.

14. The method of claim 11, wherein identifying the second plurality of characteristics of the incident includes identifying, with the electronic processor and based on the incident type, at least one of the group consisting of a type of fire, weather at the incident area, an environment surrounding the incident area, a size of a fire, a hazardous material rating at the incident area, construction characteristics of a structure at the incident area, a number of victims injured, a terrain of the incident area, and whether there is a threat of danger at the incident area.

15. The method of claim 11, further comprising:

in response to the comparison indicating that the first score is at least one of the group consisting of (i) less than the second score and (ii) less than the predetermined threshold above the second score, identifying, with the electronic processor, a third plurality of characteristics of a public safety officer, generating, with the electronic processor, a third score for the public safety officer based on the third plurality of characteristics, determining, with the electronic processor, that a combined score including a sum of the first score and the third score is greater than the predetermined threshold above the second score, and in response to determining that the combined score is greater than the predetermined threshold above the second score, transmitting, with the network interface, a list including the public safety officer to the communication device, the list being displayed by the display of the communication device.

* * * * *